United States Patent
Itsuji et al.

(10) Patent No.: US 9,452,216 B2
(45) Date of Patent: Sep. 27, 2016

(54) AGENT FOR STABILIZING ACETAMINOPHEN

(75) Inventors: Yutaka Itsuji, Osaka (JP); Yuko Itsuji, Osaka (JP); Mai Nomura, Osaka (JP); Hironori Nagahara, Osaka (JP)

(73) Assignee: MARUISHI PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 13/990,683

(22) PCT Filed: Dec. 7, 2011

(86) PCT No.: PCT/JP2011/078241
§ 371 (c)(1),
(2), (4) Date: Jun. 21, 2013

(87) PCT Pub. No.: WO2012/077696
PCT Pub. Date: Jun. 14, 2012

(65) Prior Publication Data
US 2014/0179795 A1    Jun. 26, 2014

(30) Foreign Application Priority Data
Dec. 9, 2010  (JP) .................................. 2010-274615

(51) Int. Cl.
| | |
|---|---|
| A61K 47/02 | (2006.01) |
| A61K 9/19 | (2006.01) |
| A61K 9/00 | (2006.01) |
| A61K 9/08 | (2006.01) |
| A61K 31/167 | (2006.01) |
| A61K 47/18 | (2006.01) |

(52) U.S. Cl.
CPC ............. *A61K 47/02* (2013.01); *A61K 9/0019* (2013.01); *A61K 9/08* (2013.01); *A61K 31/167* (2013.01); *A61K 47/183* (2013.01)

(58) Field of Classification Search
CPC ........... A61K 2300/00; A61K 31/167; A61K 31/485; A61K 45/06; A61K 31/192; A61K 31/165; A61K 31/137; A61K 31/38; A61K 33/06; A61K 31/415; A61K 31/135; A61K 31/16; A61K 31/505; A61K 31/60; A61K 31/01

See application file for complete search history.

(56) References Cited

U.S. PATENT DOCUMENTS

| | | | |
|---|---|---|---|
| 6,028,222 A | 2/2000 | Dietlin et al. | |
| 2003/0190307 A1 | 10/2003 | DiBiase et al. | |
| 2004/0147606 A1* | 7/2004 | Onuki et al. | ................... 514/561 |
| 2005/0148552 A1 | 7/2005 | Ryan et al. | |
| 2007/0275147 A1 | 11/2007 | Prakash et al. | |

FOREIGN PATENT DOCUMENTS

| | | |
|---|---|---|
| CN | 101791315 A | 8/2010 |
| EP | 0236822 A2 | 9/1987 |
| JP | 08-34728 A | 7/1994 |
| JP | 10-167982 | 6/1998 |
| JP | 2001519770 A | 10/2001 |
| JP | 2004067516 A | 3/2004 |
| JP | 2004123712 A | 4/2004 |
| JP | 2004269363 A | 9/2004 |
| JP | 2007510757 A | 4/2007 |
| JP | 2009517044 A | 4/2009 |
| JP | 2010163462 A | 7/2010 |
| WO | WO0168069 A2 * | 9/2001 |
| WO | WO-2009/098716 A2 | 8/2009 |
| WO | WO2009098716 A2 * | 8/2009 |

OTHER PUBLICATIONS

Rowe et al. (Handbook of Pharmaceutical Excipients (2009) 6th Ed. p. 295-296).*
Niazi (Handbook of Pharmaceutical Manufacturing Formulations: Sterile Products (2009) p. 142).*
Database WPI; Week 201075; Thomson Scientific, London, GB; AN 2010-K99602 & CN 101791315 (WANG B) Aug. 4, 2010, XP002725960.
Database WPI; Week 200864; Thomson Scientific, London, GB; AN 2008-K68044 & CN 101 062011(Shenyang Xingqi Pharmacy Co Ltd) Oct. 31, 2007; XP002725961.
Extended European Search Report in corresponding EP 11 84 7424 dated Jun. 18, 2014.
International Preliminary Report on Patentability in corresponding PCT/JP2011/078241 dated Jan. 18, 2013.
International Search Report in corresponding PCT/JP2011/078241 mailed Mar. 6, 2012.
Written Opinion in corresponding PCT/JP2011/078241 mailed Mar. 6, 2012.
International Preliminary Report on Patentability in corresponding PCT/JP2011/078241 mailed Jan. 18, 2013.

\* cited by examiner

*Primary Examiner* — Kendra D Carter
*Assistant Examiner* — Taina D Matos Negron
(74) *Attorney, Agent, or Firm* — Marshall, Gerstein & Borun LLP

(57) ABSTRACT

Provided is an agent for stabilizing acetaminophen in an aqueous composition, the agent comprising glycine. The agent further comprising at least one kind of sulfurous acid salt selected from the group consisting of sodium sulfite, potassium sulfite and potassium pyrosulfite is more effective. The stabilizing includes preventing precipitation.

10 Claims, No Drawings

AGENT FOR STABILIZING ACETAMINOPHEN

TECHNICAL FIELD

The present invention relates to an aqueous composition containing acetaminophen, an agent for stabilizing acetaminophen in an aqueous composition, and a method for stabilizing acetaminophen in an aqueous composition.

BACKGROUND ART

Acetaminophen (paracetamol) is a para-aminophenol antipyretic-analgesic agent, and is widely used for pain relief of headache, myalgia, menstrual pain, toothache and the like, and for pain relief and fever reduction in acute upper airway inflammation etc. Generally, acetaminophen is orally administered in the form of a tablet, a syrup or the like.

However, acetaminophen in an aqueous solution is unstable and susceptible to hydrolysis, which results in orange to brown discoloration.

So far, there have been various attempts to improve the stability of acetaminophen in an aqueous solution. For example, Patent Literature 1 discloses that addition of pyrosulfites such as sodium pyrosulfite to an aqueous composition containing acetaminophen improves the stability of acetaminophen.

Patent Literature 2 discloses that discoloration of an aqueous solution containing acetaminophen can be prevented by addition of polyols as a free radical scavenger, such as mannitol, sorbitol and inositol, to the aqueous solution.

However, the methods of Patent Literature 1 and 2 cannot stabilize acetaminophen to a practically sufficient degree.

Aside from these disclosures, Patent Literature 3 discloses that acetaminophen blended with glycine has an improved antipyretic action.

Patent Literature 4 discloses that aminoacetic acid (glycine) improves the antipyretic-analgesic effect of ibuprofen, a nonsteroidal antipyretic-analgesic agent.

CITATION LIST

Patent Literature

Patent Literature 1: JP-A 2004-269363
Patent Literature 2: JP-A 2010-163462
Patent Literature 3: JP-A 2004-123712
Patent Literature 4: JP-A 8-34728

SUMMARY OF INVENTION

Technical Problem

A primary object of the present invention is to provide an agent and a method for stabilizing acetaminophen to a practically sufficient degree, and an aqueous composition containing acetaminophen stabilized to a practically sufficient degree.

Solution to Problem

The present inventors conducted extensive research to achieve the above-mentioned object, and as a result, found the following.
(i) Glycine added to an aqueous composition containing acetaminophen serves to keep acetaminophen quite stable over a long period of time. Specifically, glycine prevents discoloration of the composition, precipitation in the composition, and production of acetaminophen-related substances.
(ii) A sulfurous acid salt additionally added to the composition further improves the stability of acetaminophen.

The present invention is completed based on these findings, and provides the following agents and methods for stabilizing acetaminophen, and the following aqueous compositions.

(1) An agent for stabilizing acetaminophen in an aqueous composition, the agent comprising glycine.
(2) The agent according to the above (1), further comprising a sulfurous acid salt.
(3) The agent according to the above (2), wherein the sulfurous acid salt is at least one kind selected from the group consisting of sodium sulfite, sodium hydrogen sulfite and potassium pyrosulfite.
(4) The agent according to any one of the above (1) to (3), wherein the aqueous composition is in the form of an injection.
(5) The agent according to any one of the above (1) to (4), wherein the stabilizing is preventing precipitation.
(6) A method for stabilizing acetaminophen, comprising adding glycine to an aqueous composition containing acetaminophen.
(7) The method according to the above (6), comprising further adding a sulfurous acid salt.
(8) The method according to the above (7), wherein the sulfurous acid salt is at least one kind selected from the group consisting of sodium sulfite, sodium hydrogen sulfite and potassium pyrosulfite.
(9) The method according to any one of the above (6) to (8), wherein the aqueous composition is in the form of an injection.
(10) The method according to any one of the above (6) to (9), wherein the stabilizing is preventing precipitation.
(11) An aqueous composition comprising acetaminophen, glycine and a sulfurous acid salt.
(12) The aqueous composition according to the above (11), wherein the sulfurous acid salt is at least one kind selected from the group consisting of sodium sulfite, sodium hydrogen sulfite and potassium pyrosulfite.
(13) The aqueous composition according to the above (11) or (12), wherein the pH of the aqueous composition is 4 to 7.
(14) The aqueous composition according to any one of the above (11) to (13), which is in the form of an injection.
(15) Use of glycine for production of an agent for stabilizing acetaminophen in an aqueous composition.
(16) Glycine for use in stabilization of acetaminophen in an aqueous composition.

Advantageous Effects of Invention

The agent of the present invention which comprises glycine can effectively stabilize acetaminophen when used as an additive in an aqueous composition containing acetaminophen. Specifically, even in a prolonged storage of such an aqueous composition at a relatively high temperature, the agent can effectively prevent discoloration of the aqueous composition, production of acetaminophen-related substances (for example, acetaminophen degradation products) in the aqueous composition, and precipitation in the aqueous composition. This makes it easier to store aqueous formulations containing acetaminophen, and paves the way for the development of new dosage forms of acetaminophen.

DESCRIPTION OF EMBODIMENTS

Hereinafter, the present invention will be illustrated in detail.

(I) Stabilizing Agent

According to the present invention, the agent for stabilizing acetaminophen comprises glycine as an active ingredient. As used herein, "stabilizing" includes preventing discoloration, production of acetaminophen-related substances, or precipitation. That is, the agent for stabilizing acetaminophen includes agents for preventing discoloration of acetaminophen, production of acetaminophen-related substances, or precipitation. The possible causes of the discoloration of acetaminophen include oxidation and hydrolysis. The acetaminophen-related substances include acetaminophen degradation products. The stabilizing agent of the present invention, which prevents discoloration of acetaminophen, also prevents discoloration of an aqueous composition containing acetaminophen.

Acetaminophen

Acetaminophen (N-(4-hydroxyphenyl)acetamide) is listed in the Japanese pharmacopoeia, 15th edition, and commercially available.

The concentration of acetaminophen in an aqueous composition can be, for example, about 0.1 to 5 w/v %, and is preferably about 0.1 to 2 w/v %.

Glycine

The agent of the present invention which comprises glycine as an active ingredient is used as an additive in an aqueous composition containing acetaminophen. The aqueous composition containing acetaminophen is preferably in the form of an injection.

When the amount of glycine used in the aqueous composition is such that the glycine concentration in the aqueous composition is about 0.01 w/v % or higher, the effects of the present invention can be sufficiently achieved. In particular, the glycine concentration in the aqueous composition is preferably about 0.01 to 20 w/v %, more preferably about 0.01 to 5 w/v %, further more preferably about 0.05 to 2 w/v %, and still more preferably about 0.1 to 1 w/v %. The amount of glycine used relative to 1 part by weight of acetaminophen is preferably about 0.01 to 5 parts by weight, more preferably about 0.05 to 2 parts by weight, and further more preferably about 0.1 to 1 part by weight. When the amount of glycine is in the above range, acetaminophen can be sufficiently stabilized. When the amount of glycine is in the above range, glycine can be sufficiently dissolved in the aqueous composition.

Sulfurous Acid Salt

It is preferable that the agent of the present invention further comprises a sulfurous acid salt, and such an agent can more effectively stabilize acetaminophen in an aqueous composition.

Examples of the sulfurous acid salt include sulfites, hydrogen sulfites and pyrosulfites. Examples of the salt include a sodium salt and a potassium salt. Inter alia, preferred are sodium sulfite, sodium hydrogen sulfite and potassium pyrosulfite. The sulfurous acid salt used may be a single compound or a combination of two or more compounds. As the sulfurous acid salt, commercial products can be used.

The amount of the sulfurous acid salt used, i.e., the amount of the sulfurous acid salt added to the aqueous composition, is such that the concentration of the sulfurous acid salt in the aqueous composition is preferably about 0.01 to 0.1 w/v %, more preferably about 0.03 to 0.1 w/v %, and further more preferably about 0.03 to 0.05 w/v %. The amount of the sulfurous acid salt used relative to 1 part by weight of acetaminophen is preferably about 0.01 to 0.1 part by weight, more preferably about 0.03 to 0.1 part by weight, and further more preferably about 0.03 to 0.05 part by weight. When the amount of the sulfurous acid salt is in the above range, acetaminophen can be sufficiently stabilized. When the amount of the sulfurous acid salt is in the above range, the sulfurous acid salt can be sufficiently dissolved in the aqueous composition.

Isotonizing Agent

The agent of the present invention can comprise an isotonizing agent.

Examples of the isotonizing agent include sugars such as trehalose, glucose, fructose and sucrose; sugar alcohols such as xylitol, sorbitol, inositol, mannitol and erythritol; and sodium chloride.

The amount of the isotonizing agent used, i.e., the amount of the isotonizing agent added to the aqueous composition, is such that the aqueous composition becomes isotonic, and can be determined by the skilled person depending on the kind of the isotonizing agent.

(II) Aqueous Composition

The aqueous composition of the present invention comprises acetaminophen, glycine and a sulfurous acid salt. Acetaminophen, glycine, the kind of the sulfurous acid salt, and the amounts of them used in the aqueous composition are as described above. Preferably, the aqueous composition of the present invention further comprises the isotonizing agent described above. The kind and the amount of the isotonizing agent used are as described above.

pH

The pH of the aqueous composition of the present invention is preferably about 4 to 7, more preferably about 5 to 6, and further more preferably about 5. When the pH of the aqueous composition is in the above range, acetaminophen can be effectively stabilized.

The pH of the aqueous composition can be adjusted with the use of organic acids, such as citric acid, malic acid, tartaric acid and lactic acid, as well as inorganic compounds, such as NaOH, KOH, HCl and $H_3PO_4$. Inter alia, preferably used are organic acids, and more preferably used is citric acid.

Dosage Form

The aqueous composition of the present invention is usually a pharmaceutical composition or a quasi-drug composition. Exemplary dosage forms include oral preparations (emulsions, solutions, suspensions, syrups, jellies, etc.), injections, and external preparations (solutions, suspensions, emulsions, gels, liniments, lotions, etc.). Inter alia, preferred are injections.

The oral preparations can be prepared by dissolving or dispersing the above-described active ingredients including glycine in a solvent such as water, ethanol, glycerin, simple syrup and a mixture thereof. The oral preparations may further contain an additive such as a sweetener, a preservative, a buffering agent, a flavor and a colorant.

The injections can be obtained by dissolving or dispersing the above-described active ingredients including glycine in distilled water for injection, physiological saline or the like. The injections may further contain an additive such as a buffering agent, a stabilizing agent, a soothing agent and a preservative.

The external preparations can be prepared by blending the above-described active ingredients including glycine with a suitable base. Examples of the base include polymers such as sodium alginate, gelatin, cornstarch, tragacanth gum, methyl cellulose, hydroxyethyl cellulose, carboxymethyl cellulose, xanthan gum, carrageenan, mannan, agarose, dextrin, carboxymethyl starch, polyvinyl alcohol, sodium polyacrylate, a methoxyethylene-maleic anhydride copolymer, polyvinyl ether, polyvinyl pyrrolidone, a carboxyvinyl polymer, hydroxypropyl cellulose, hydroxypropyl methyl cellulose and pullulan; hydrocarbons such as white petrolatum, yellow petrolatum, paraffin, ceresin wax and microcrystalline wax; gelled hydrocarbons, for example, Plastibase (trade name, manufactured by Bristol-Myers Squibb Company); higher fatty acids such as stearic acid; higher alcohols such as cetanol, octyl dodecanol and stearyl alcohol; polyethylene glycol, for example, macrogol 4000 etc.; polyhydric alcohols such as propylene glycol, glycerin, dipropylene glycol, 1,3-butylene glycol and concentrated glycerin; fatty acid esters such as monoesters of oleic acid and stearic acid glyceride; and a phosphate buffer solution. The external preparations may further contain an additive such as a solubilizer, an inorganic filler, a moisturizer, a preservative, a thickener, an antioxidant and a refrigerant.

In the aqueous composition of the present invention, the base used may be a single base or a combination of two or more bases, and the same shall apply to the additive.

The "aqueous composition" as used herein refers to a composition containing water, and the water content of the aqueous composition is preferably about 20 v/v % or higher, more preferably about 50 v/v % or higher, and further more preferably about 90 v/v % or higher relative to the total volume of the composition.

(III) Stabilizing Method

The present invention includes a method for stabilizing acetaminophen, comprising adding glycine to an aqueous composition containing acetaminophen. As used herein, "stabilizing" includes preventing discoloration of acetaminophen, production of acetaminophen-related substances, or precipitation.

The details of this method are as described regarding the stabilizing agent of the present invention. In brief, the concentration of acetaminophen in the aqueous composition can be, for example, about 0.1 to 5 w/v %, and is preferably about 0.1 to 2 w/v %.

When the amount of glycine added to the aqueous composition is such that the glycine concentration in the aqueous composition is about 0.01 w/v % or higher, the effects of the present invention can be sufficiently achieved. In particular, the glycine concentration in the aqueous composition is preferably about 0.01 to 20 w/v %, more preferably about 0.01 to 5 w/v %, further more preferably about 0.05 to 2 w/v %, and still more preferably about 0.1 to 1 w/v %. The amount of glycine used relative to 1 part by weight of acetaminophen is preferably about 0.01 to 5 parts by weight, more preferably about 0.05 to 2 parts by weight, and further more preferably about 0.1 to 1 part by weight. When the amount of glycine is in the above range, acetaminophen can be sufficiently stabilized. When the amount of glycine is in the above range, glycine can be sufficiently dissolved in the aqueous composition.

The method of the present invention preferably comprises adding a sulfurous acid salt as well as glycine to an aqueous composition containing acetaminophen, and such a method can more effectively stabilize acetaminophen.

Examples of the sulfurous acid salt include sulfites, hydrogen sulfites and pyrosulfites. Examples of the salt include a sodium salt and a potassium salt. Inter alia, preferred are sodium sulfite, sodium hydrogen sulfite and potassium pyrosulfite. The sulfurous acid salt used may be a single compound or a combination of two or more compounds.

The amount of the sulfurous acid salt added to the aqueous composition is such that the concentration of the sulfurous acid salt in the aqueous composition is preferably about 0.01 to 0.1 w/v %, more preferably about 0.03 to 0.1 w/v %, and further more preferably about 0.03 to 0.05 w/v %. The amount of the sulfurous acid salt used relative to 1 part by weight of acetaminophen is preferably about 0.01 to 0.1 part by weight, more preferably about 0.03 to 0.1 part by weight, and further more preferably about 0.03 to 0.05 part by weight. When the amount of the sulfurous acid salt is in the above range, acetaminophen can sufficiently be stabilized. When the amount of the sulfurous acid salt is in the above range, the sulfurous acid salt can be sufficiently dissolved in the aqueous composition.

The aqueous composition is usually a pharmaceutical composition or a quasi-drug composition. Exemplary dosage forms include oral preparations (emulsions, solutions, suspensions, syrups, jellies, etc.), injections, and external preparations (solutions, suspensions, emulsions, gels, liniments, lotions, etc.). Inter alia, preferred are injections.

EXAMPLES

Hereinafter, the present invention will be illustrated in more detail by Examples, but is not limited thereto.

(1) Stability Under High-Temperature and High-Pressure Conditions

Aqueous compositions containing glycine at the concentrations shown in Table 1 below, 1 w/v % acetaminophen, 5 w/v % xylitol and phosphoric acid (q.s.) and having the pH of 5 were heat-treated at 121° C. for 1 hour, and subsequently visually observed in terms of the color tone (the degree of discoloration) and the presence of precipitates.

In addition, the concentration of acetaminophen-related substances in each aqueous composition was determined by HPLC. The HPLC conditions were as follows.

<HPLC Conditions>

The analysis was performed using liquid chromatography as described in the purity test of acetaminophen (related substances) prescribed in the manual of the Japanese pharmacopoeia, 15th edition. That is, each solution was subjected to HPLC using an octadecyl silica gel column and a mobile phase prepared by mixing methanol and a potassium dihydrogen phosphate solution, the peak areas at the detection wavelength of 225 nm were determined by an automatic integration method, and the percentage of the summed peak areas of the related substances to the total area of all peaks (total amount of related substances (%)) was calculated.

The results are shown in Table 1 below.

TABLE 1

| <Stability at various glycine concentrations under high-temperature and high-pressure conditions (121° C., 1-hour treatment)> | | | | |
|---|---|---|---|---|
| | 0 w/v % | 0.14 w/v % | 0.28 w/v % | 0.56 w/v % |
| Color tone | + | − | − | − |
| Precipitation | − | − | − | − |
| Total amount of related substances (%) | 0.33 | 0.03 | 0.01 | 0 |

The symbols and the numerical values in the tables of the present description represent the following.
Color Tone:
  +++: deep brown
  ++: slightly deep brown
  +: light brown
  ±: very little discoloration
  −: no discoloration
Precipitation:
  +: visible precipitates
  −: no precipitates
Total amount of related substances (%): the percentage of the summed peak areas of the related substances to the total area of all peaks (2) Stability in Long-Term Storage Under Extreme Conditions The acetaminophen-containing aqueous solutions described below were prepared, autoclaved at 121° C. for 20 minutes, and stored at 60° C. for 21 days. Subsequently, the aqueous solutions were visually observed in terms of the color tone (the degree of discoloration) and the presence of precipitates. In addition, the concentration of acetaminophen-related substances in each aqueous solution was determined by HPLC.

A glycine solution contains glycine as a stabilizing agent, physiological saline does not contain glycine, and perfalgan (registered trademark) is a commercial acetaminophen-containing injection, which contains cysteine hydrochloride.
Physiological Saline:
  acetaminophen 1 w/v %, NaCl 0.9 w/v %, pH=5.75
Glycine Solution:
  acetaminophen 1 w/v %, NaCl 0.9 w/v %, glycine 0.56 w/v %, pH=5.88
Perfalgan:
  acetaminophen 1 w/v %, cysteine hydrochloride monohydrate 0.025 w/v %, disodium hydrogen phosphate dihydrate 0.013 w/v %, mannitol 3.85 w/v %, NaOH and HCl q.s.

The results are shown in Table 2 below.

TABLE 2

<Comparison of stability under extreme conditions (60° C., 21-day storage) between glycine solution and overseas product>

|  | Physiological saline | Glycine solution | Perfalgan* |
|---|---|---|---|
| Color tone | + | + | ++ |
| Precipitation | + | − | + |
| Total amount of related substances (%) | 3.2 | 0.07 | 0.04 |

*The commercial perfalgan vial was freshly opened, and aliquots were prepared and used for the storage test under extreme conditions.

In the glycine solution, precipitation was prevented and the total amount of the related substances was kept low even under extreme conditions (60° C.). Further, in the glycine solution, discoloration was observed after 21 days of storage, but the color tone was lighter than that of perfalgan.

(3) Stability in the Presence of Sodium Sulfite in Long-Term Storage Under Extreme Conditions The acetaminophen-containing aqueous solutions described below were prepared, autoclaved at 121° C. for 20 minutes, and stored at 60° C. for 21 days. Subsequently, the aqueous solutions were visually observed in terms of the color tone (the degree of discoloration) and the presence of precipitates. In addition, the concentration of acetaminophen-related substances in each aqueous solution was determined by HPLC.
Glycine solution+citric acid (pH=6):
  acetaminophen 1 w/v %, glycine 0.56 w/v %, citric acid 0.22 w/v %, NaCl 0.9 w/v %, NaOH q.s., pH=6.0
Glycine Solution+Citric Acid+Sodium Sulfite (pH=6):
  acetaminophen 1 w/v %, glycine 0.56 w/v %, citric acid 0.22 w/v %, sodium sulfite 0.03 w/v %, NaCl 0.9 w/v %, NaOH q.s., pH=6.0

The results are shown in Table 3 below.

TABLE 3

<Comparison of stability under extreme conditions (60° C., 21-day storage) between glycine solutions (with or without sodium sulfite)>

|  | Glycine solution + citric acid (pH 6) | Solution in left column + sodium sulfite (pH 6) |
|---|---|---|
| Color tone | + | − |
| Precipitation | − | − |
| Total amount of related substances (%) | 0.05 | 0.01 |

In the presence of both of glycine and sodium sulfite, discoloration was prevented.

(4) Effects of pH

Aqueous solutions with the pHs shown in Table 4 below were prepared by mixing 1 w/v % of acetaminophen, 0.56 w/v % of glycine, 0.22 w/v % of citric acid, 0.9 w/v % of NaCl, and NaOH or $H_3PO_4$ (q.s.). The aqueous solutions were autoclaved at 121° C. for 20 minutes and then stored at 60° C. for 21 days. Subsequently, the aqueous solutions were visually observed in terms of the color tone (the degree of discoloration) and the presence of precipitates. In addition, the concentration of acetaminophen-related substances in each aqueous solution was determined by HPLC.

The results are shown in Table 4 below.

TABLE 4

<Effects of pH under extreme conditions (60° C., 21-day storage)>

| pH | 2 | 3 | 4 | 5 | 6 | 7 | 8 |
|---|---|---|---|---|---|---|---|
| Color tone | +++ | ++ | ± | ± | + | ++ | +++ |
| Precipitation | + | + | + | − | − | − | + |
| Total amount of related substances (%) | 12.18 | 5.44 | 0.8 | 0.05 | 0.05 | 0.06 | 0.07 |

The results show that the optimal pH for stabilization of acetaminophen was 4 to 7, and in particular, 5 to 6.

INDUSTRIAL APPLICABILITY

Glycine effectively prevents degradation, oxidation and other modifications of acetaminophen in an aqueous composition, discoloration of the aqueous composition and precipitation in the aqueous composition.

The invention claimed is:
1. A composition for stabilizing acetaminophen in an aqueous composition, the composition comprising glycine and sodium sulfite, the composition being used so that the amount of glycine is about 0.1 to 5 parts by weight relative to 1 part by weight of acetaminophen and the amount of sodium sulfite is about 0.01 to 0.1 part by weight relative to 1 part by weight of acetaminophen.

2. The composition according to claim 1, wherein the aqueous composition is in the form of an injection.

3. The composition according to claim 1, wherein the stabilization prevents precipitation of acetaminophen.

4. A method for stabilizing acetaminophen, comprising adding glycine and sodium sulfite to an aqueous composition containing acetaminophen, wherein the amount of glycine is about 0.1 to 5 parts by weight relative to 1 part by weight of acetaminophen, and wherein the amount of sodium sulfite is about 0.01 to 0.1 part by weight relative to 1 part by weight of acetaminophen.

5. The method according to claim 4, wherein the aqueous composition is in a form suitable for injection.

6. The method according to claim 4, wherein the stabilization prevents precipitation of acetaminophen.

7. An aqueous composition comprising acetaminophen, glycine and sodium sulfite, wherein the amount of glycine is about 0.1 to 5 parts by weight relative to 1 part by weight of acetaminophen, and wherein the amount of sodium sulfite is about 0.01 to 0.1 part by weight relative to 1 part by weight of acetaminophen.

8. The aqueous composition according to claim 7, wherein the pH of the aqueous composition is 4 to 7.

9. The aqueous composition according to claim 7, which is in a form suitable for injection.

10. A composition comprising glycine and sodium sulfite for use in stabilization of acetaminophen in an aqueous composition, the composition being used so that the amount of glycine is about 0.1 to 5 parts by weight relative to 1 part by weight of acetaminophen and the amount of sodium sulfite is about 0.01 to 0.1 part by weight relative to 1 part by weight of acetaminophen.

* * * * *